United States Patent [19]

Furuya et al.

[11] Patent Number: 5,567,699

[45] Date of Patent: Oct. 22, 1996

[54] THIADIAZINONE DERIVATIVES

[75] Inventors: Rikizo Furuya; Hiromi Okushima; Yuji Abe, all of Kanagawa, Japan

[73] Assignee: Mitsubishi Chemical Corporation, Tokyo, Japan

[21] Appl. No.: 422,916

[22] Filed: Apr. 17, 1995

[30] Foreign Application Priority Data

Apr. 26, 1994 [JP] Japan ................................. 6-088509

[51] Int. Cl.$^6$ ..................... C07D 285/16; A61K 31/54
[52] U.S. Cl. ............................. 514/222.5; 544/8
[58] Field of Search ....................... 544/8; 514/222.5

[56] References Cited

U.S. PATENT DOCUMENTS

| | | | |
|---|---|---|---|
| 4,661,484 | 4/1987 | Okushima et al. | 514/242 |
| 4,822,797 | 4/1989 | Okushima et al. | 514/252 |
| 4,971,968 | 11/1990 | Okushima et al. | 514/242 |

FOREIGN PATENT DOCUMENTS

| | | |
|---|---|---|
| 0052442 | 5/1982 | European Pat. Off. . |
| 0085985 | 8/1983 | European Pat. Off. . |
| 0252422 | 1/1988 | European Pat. Off. . |
| 0383449 | 8/1990 | European Pat. Off. . |
| 0539806 | 5/1993 | European Pat. Off. . |
| 58-8015 | 1/1983 | Japan . |
| 58-8016 | 1/1983 | Japan . |
| 58-148865 | 9/1983 | Japan . |
| 58-203978 | 11/1983 | Japan . |
| 58-188815 | 11/1983 | Japan . |
| 58-203977 | 11/1983 | Japan . |
| 58-183618 | 10/1983 | Japan . |
| 50-84883 | 5/1984 | Japan . |
| 60-87283 | 5/1985 | Japan . |
| 60-197681 | 10/1985 | Japan . |
| 61-183282 | 8/1986 | Japan . |
| 63-154670 | 6/1988 | Japan . |
| 2-59571 | 2/1990 | Japan . |
| 2-59573 | 2/1990 | Japan . |
| 2-59574 | 2/1990 | Japan . |
| 2-59577 | 2/1990 | Japan . |
| 3-261773 | 11/1991 | Japan . |

OTHER PUBLICATIONS

Moersdorf et al, Chemical Abstracts, vol. 114, entry 122426 (1990).

*Primary Examiner*—John M. Ford
*Attorney, Agent, or Firm*—Wenderoth, Lind & Ponack

[57] ABSTRACT

This invention provides thiadiazinone derivatives represented by the following formula (I)

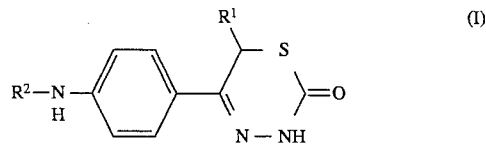

wherein $R^1$ represents a hydrogen atom or $C_1$–$C_5$ alkyl, $R^2$ represents a 5- or 6-membered heterocyclic ring having (a) 1–3 nitrogen atoms, (b) a oxygen atom, (c) one sulfur atom, (d) 1–3 nitrogen atoms and one oxygen atom, or (e) 1–3 nitrogen atoms and one sulfur atom each of which rings may optionally be substituted by at least one substituent selected from the group consisting of $C_1$–$C_5$ alkyl, cyano, hydroxy, $C_1$–$C_5$ alkoxy, amino, $C_1$–$C_5$ alkylamino, $C_2$–$C_6$ dialkylamino, $C_2$–$C_5$ acylamino, carboxyl, $C_2$–$C_5$ alkoxycarbonyl and carbamoyl; or a pharmaceutically acceptable salt thereof. The compounds according to the present invention have an excellent cardiotonic activity, and are useful as active ingredients of a cardiotonic drug.

7 Claims, No Drawings

THIADIAZINONE DERIVATIVES

BACKGROUND OF THE INVENTION

1. Field of the Invention

The present invention relates to novel thiadiazinone derivatives or salts thereof which are useful as a cardiotonic drug.

2. Discussion of the Background

Cardiotonic drugs directly act on the heart and promote its contraction. Various kinds of the drugs have been conventionally utilized for the treatment of heart failure.

Examples of the drugs which are known to have a cardiotonic activity and have been conventionally utilized are as follows: pyridazinone derivatives (Japanese Laid-Open Patent Publication Nos. 8015/83, 8016/83, 87283/85, 183282/86, 154670/88, 148865/83, 183618/83, 203978/83 and 84883/84, U.S. Pat. Nos. 4661484 and 4971968, European Laid-Open Patent Publication No. 85985, and the like); pyridazine-3-thione derivatives (Japanese Patent Nos. 188815/83 and 203977/83, and the like); pyridine derivatives (Japanese Laid-Open Patent Publication No. 197681/85, and the like); pyridone derivatives (Japanese Laid-Open Patent Publication No.59571/90 and the like); 2(1H)-pyrimidinone derivatives (Japanese Laid-Open Patent Publication No.59573/90, and the like); pyradinone derivatives (Japanese Laid-Open Patent Publication No. 59574/90); and thiazolone derivatives (Japanese Patent No. 59577/90, and the like).

However, the conventionally-used cardiotonic drugs as stated above have the following disadvantages: they have very narrow safety margins; they can cause arrhythmia; their cardiotonic action is transient; and they are not suitable for oral administration.

SUMMARY OF THE INVENTION

An object of the invention is to provide a novel cardiotonic drug which has a wide safety margin and which is satisfactorily applicable for clinical use.

The inventors have earnestly studied to overcome the above-mentioned disadvantages and have found that thiadiazinone derivatives having a specific heterocyclic ring or salts thereof have an excellent cardiotonic action.

The present invention resides in thiadiazinone derivatives represented by the following formula (I).

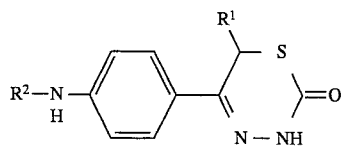

(I)

wherein $R^1$ represents a hydrogen atom or $C_1$–$C_5$ alkyl, $R^2$ represents a 5- or 6-membered heterocyclic ring having (a) 1–3 nitrogen atoms, (b) one oxygen atom, (c) one sulfur atom, (d) 1–3 nitrogen atoms and one oxygen atom, or (e) 1–3 nitrogen atoms and one sulfur atom and each of which rings may be substituted by at least one substituent selected from the group consisting of $C_1$–$C_5$ alkyl, cyano, hydroxy, $C_1$–$C_5$ alkoxy, amino, $C_1$–$C_5$ alkylamino, $C_2$–$C_6$ dialkylamino, $C_2$–$C_5$ acylamino, carboxyl, $C_2$–$C_5$ alkoxycarbonyl and carbamoyl; or pharmaceutically acceptable salts thereof.

According to the present invention, there are also provided pharmaceutical compositions comprising the compounds of formula (I) and a pharmaceutically acceptable carrier; and a cardiotonic drug comprising the compounds of formula (I) as an effective ingredient.

DETAILED DESCRIPTION OF THE PREFERRED EMBODIMENT

The invention will be described in detail as follows. $R^2$ of the formula (I) is described in detail;

examples of the 5- or 6-membered heterocyclic ring having 1–3 nitrogen atoms are pyridyl, pyridazinyl, pyrimidinyl, pyrazinyl, s-triazinyl, pyrrolyl, imidazolyl, pyrazolyl, pyrrolidinyl, pyrrolinyl, imidazolidinyl, imidazolinyl, pyrazolidinyl, pyrazolinyl, piperidyl and piperadinyl, examples of the 5- or 6-membered heterocyclic ring having one oxygen atom are furyl, pyranyl, tetrahydrofuryl and tetrahydropyranyl, an example of the 5- or 6-membered heterocyclic ring having one sulfur atom is thienyl, examples of the 5- or 6-membered heterocyclic ring having nitrogen atoms and one oxygen atom are oxazolyl, isooxazolyl, furazanyl, and morpholinyl, examples of the 5- or 6-membered heterocyclic ring having 1–3 nitrogen atoms and one sulfur atom are thiazolyl and isothiazolyl.

Each of said heterocyclic rings of $R^2$ as defined above may optionally be substituted by at least one substituent(s) selected from a group consisting of $C_1$–$C_5$ alkyl such as methyl, ethyl, n-propyl, i-propyl, n-butyl, t-butyl and n-pentyl; cyano; hydroxy; $C_1$–$C_5$ alkoxy such as methoxy, ethoxy, n-propoxy, i-propoxy, n-butyloxy, t-butyloxy and n-pentyloxy; amino; $C_1$–$C_5$ alkylamino such as methylamino, ethylamino, n-propylamino, i-propylamino, n-butylamino and n-pentylamino; $C_2$–$C_6$ dialkylamino such as dimethylamino, methylethylamino and diethylamino; $C_2$–$C_5$ acylamino such as alkanoylamino, e.g., acetylamino, propionylamino and butyrylamino; carboxyl; $C_2$–$C_5$ alkoxycarbonyl such as methoxycarbonyl, ethoxycarbonyl, n-propoxycarbonyl, i-propoxycarbonyl and n-butoxycarbonyl; and carbamoyl.

Examples of said $C_1$–$C_5$ alkyl of $R^1$ are as defined above.

Groups which are not specifically provided for in said description for definition of $R^1$ and $R^2$ can be selected by optional combinations based on the above atoms and groups or according to general knowledge in the art.

In the formula (I) of thiadiazinone derivatives according to the present invention, $R^2$ is preferably a 5- or 6-membered heterocyclic ring having 1–3 nitrogen atoms each ring of which may optionally be substituted by at least one substituent as described above. Most preferred are the 5- or 6-membered heterocyclic ring having 1–3 nitrogen atoms each ring of which has no substituent, the 5- or 6-membered heterocyclic ring having one nitrogen atom or the 6-membered heterocyclic ring having 1–3 nitrogen atoms. Pyridyl is most preferable for the heterocyclic ring of $R^2$. $R^1$ is preferably a hydrogen atom or methyl.

The thiadiazinone derivatives of the formula (I) according to the invention may form pharmaceutically acceptable salts. When an acidic group is present, examples of the salts are metal salts such as lithium salts, sodium salts, potassium salts, magnesium salts, and calcium salts; and ammonium salts such as ammonium salts; methylammonium salts, dimethylammonium salts, trimethylammonium salts, and dicyclohexylammonium salts. When a basic group is present, examples of the salts are mineral acid salts such as hydrochlorides, hydrobromides, sulfates, nitrates, and phosphates; organic acid salts such as methanesulfonates, benzenesulfonates, paratoluenesulfonates, acetates, propionates, tartrates, fumarates, maleates, malates, borates, succinates, citrates, benzoates, mandelates, cinnamates, and lactates.

When $R^1$ of the formula (I) is $C_1$–$C_5$ alkyl and the derivatives automatically have an asymmetric carbon, the thiadiazinone derivatives according to the present invention include all of the (R), (S) and (RS) forms.

Specific compounds included in the thiadiazinone derivatives of the present invention represented by the formula (I) are exemplified as follows:

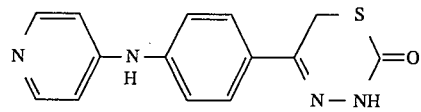

(Example 1)

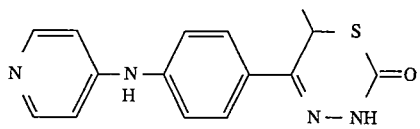

(Example 2)

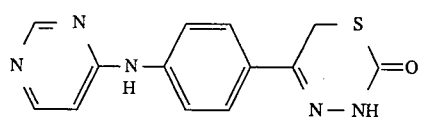

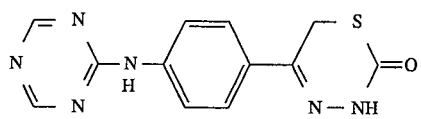

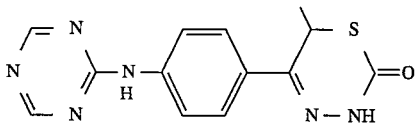

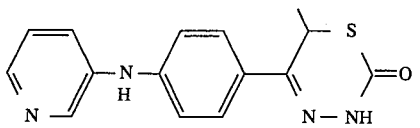

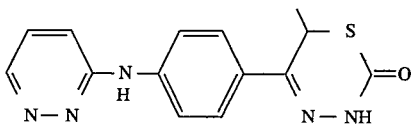

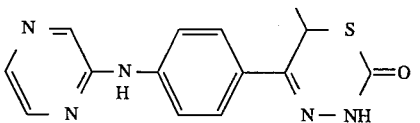

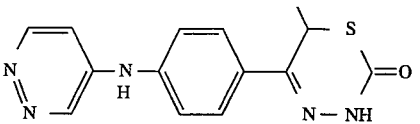

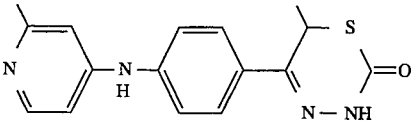

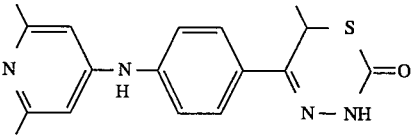

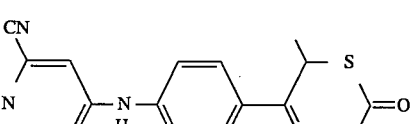

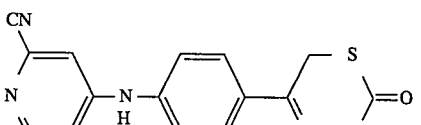

5
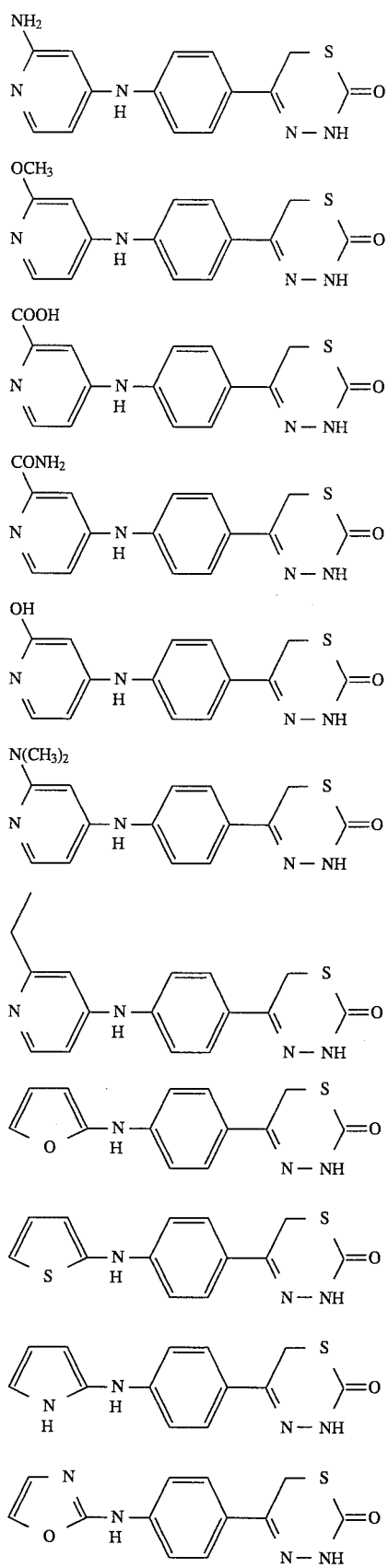
6
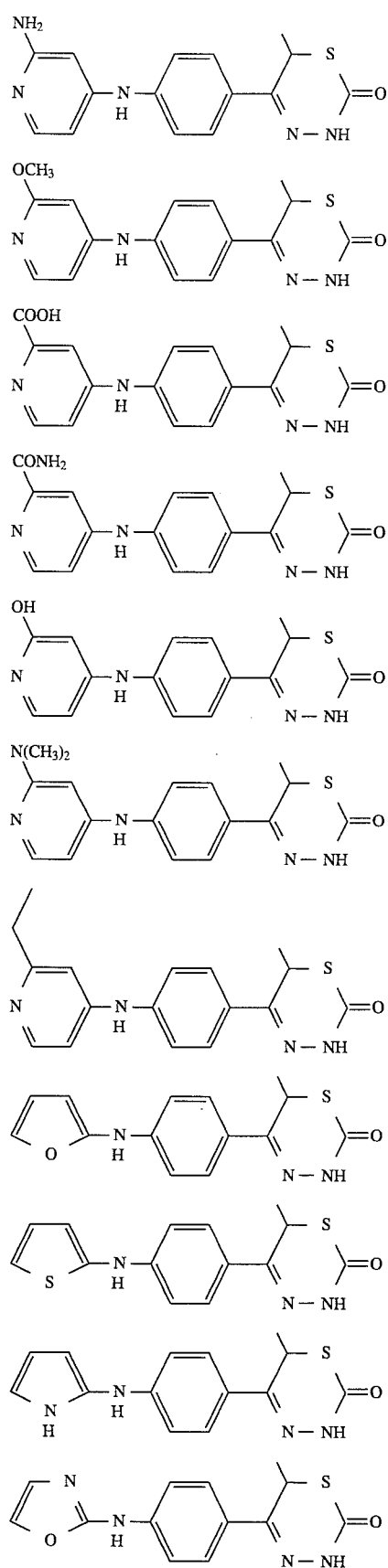

-continued
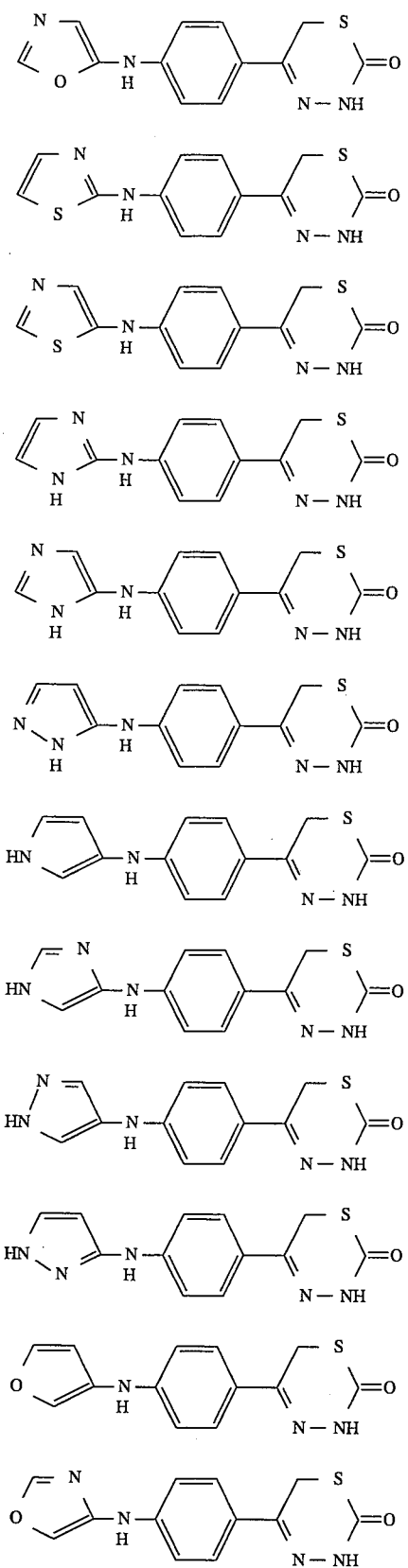
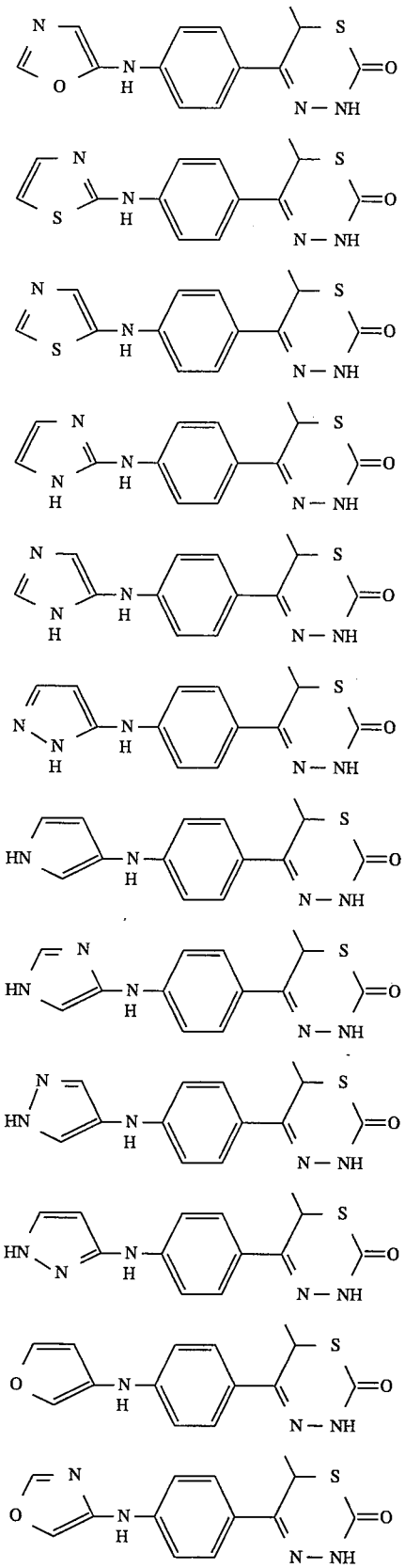

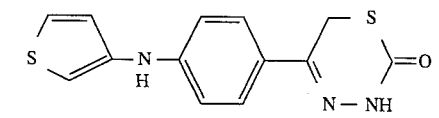
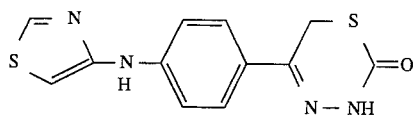
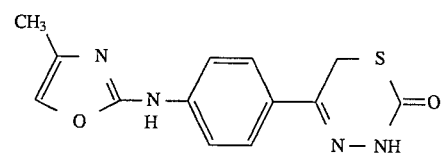
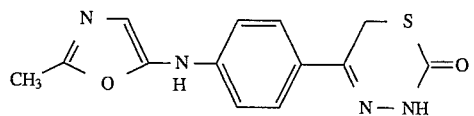
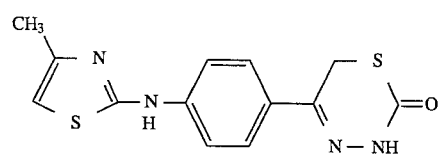
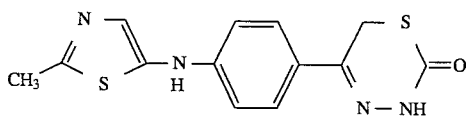
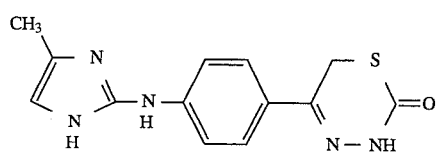
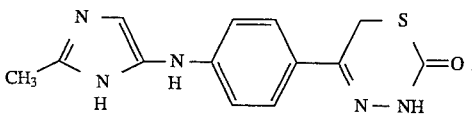
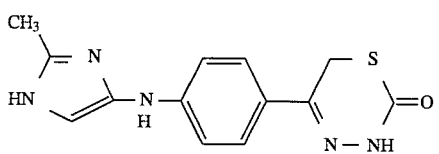
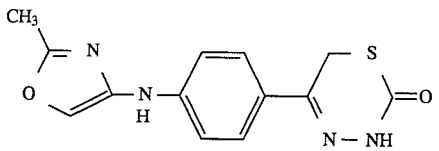
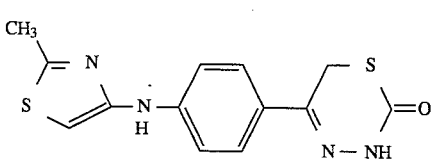
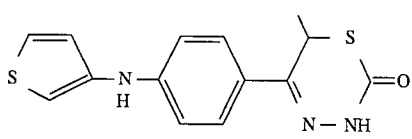
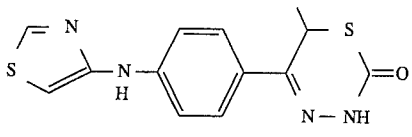
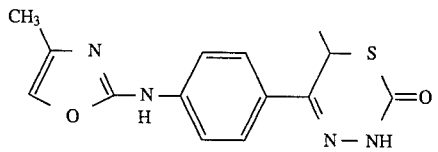
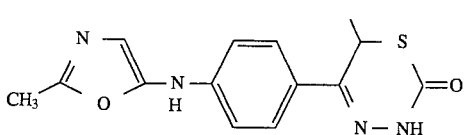
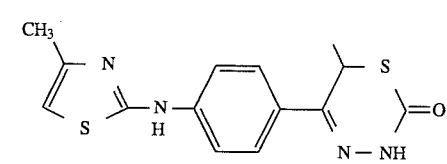
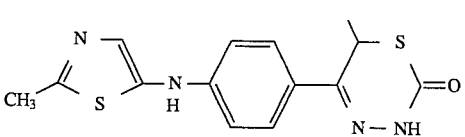
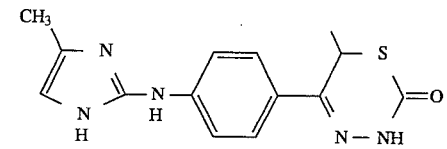
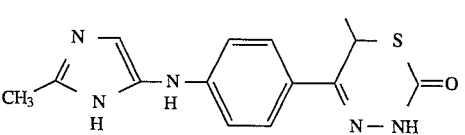
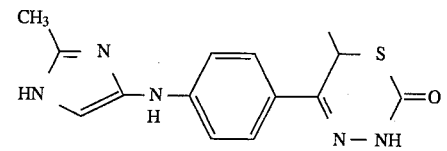
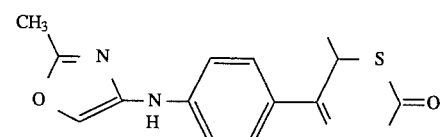
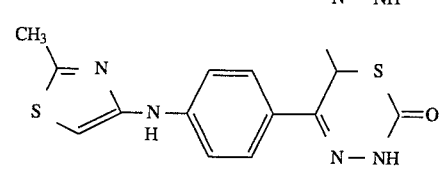

11
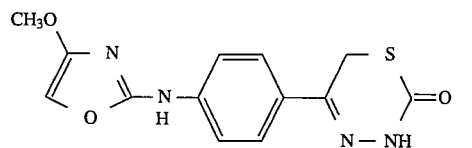
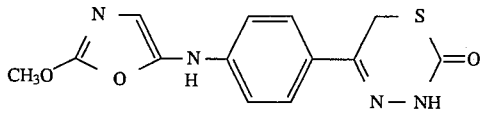
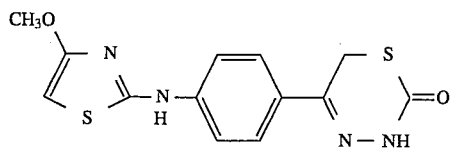
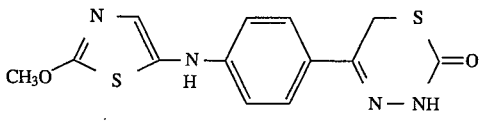
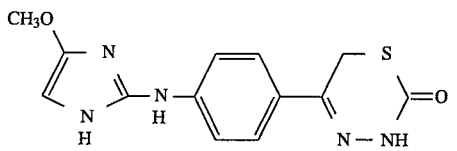
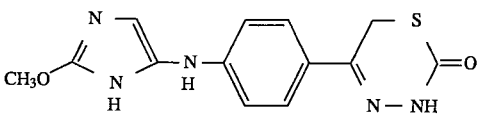
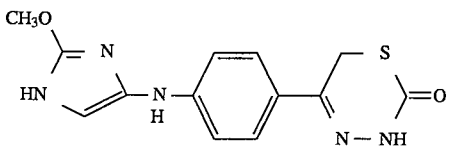
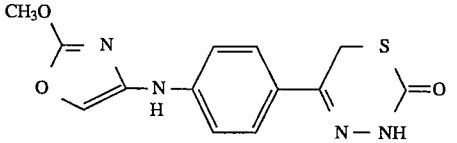
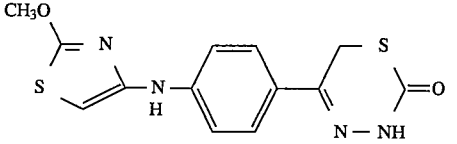
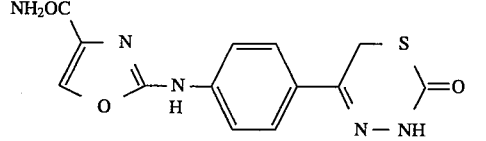
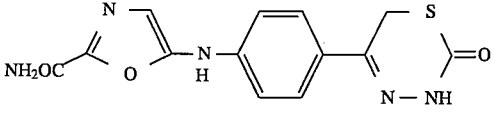
12
-continued
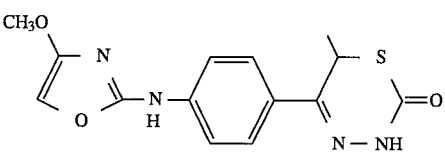
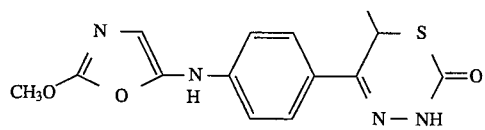
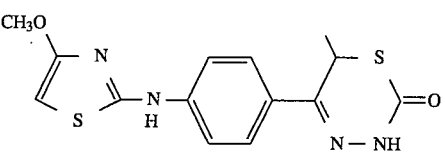
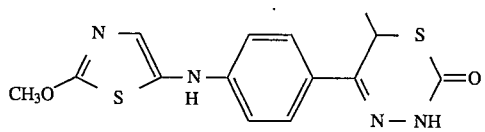
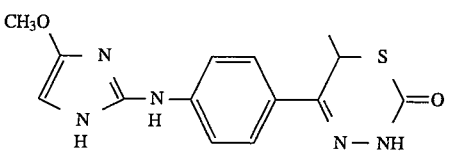
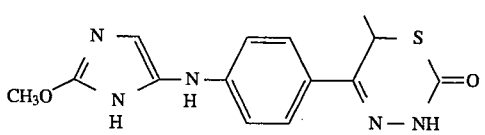
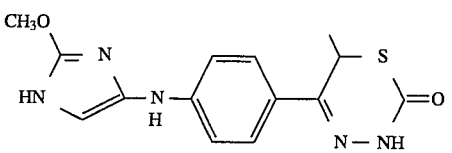
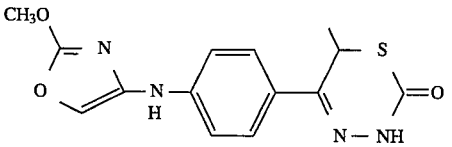
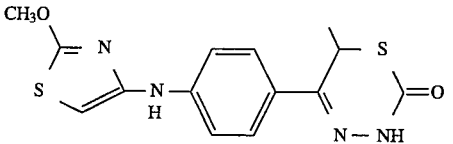
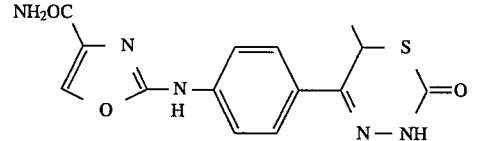
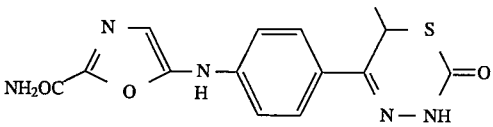

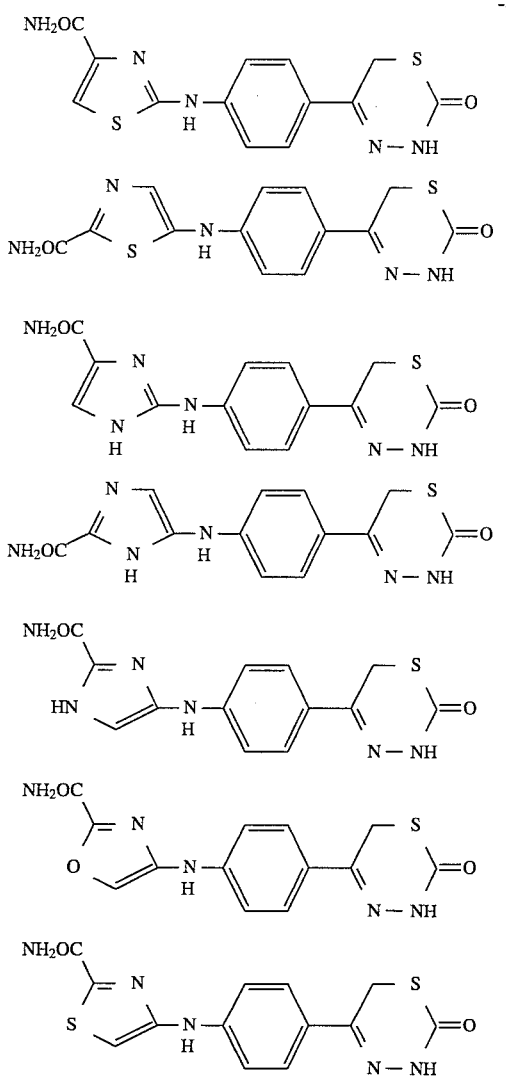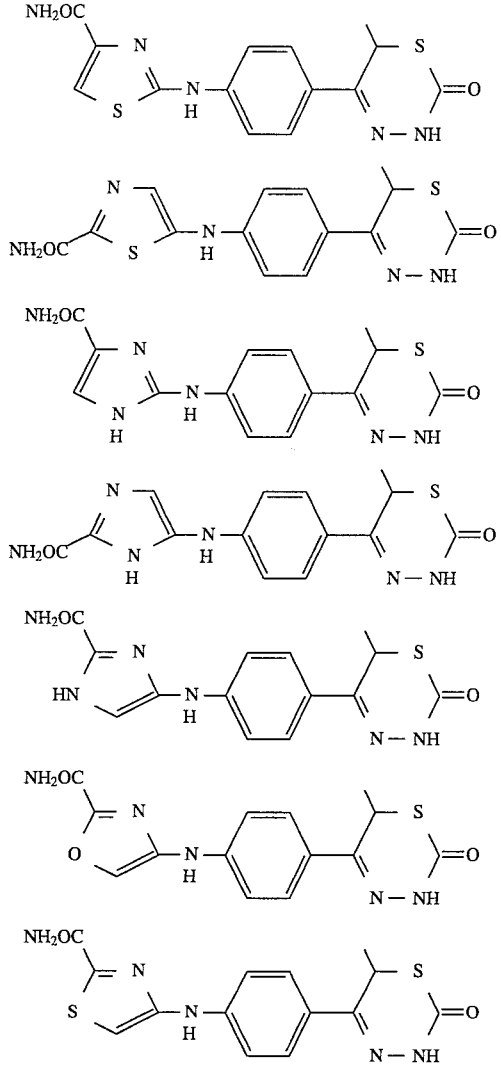

Thiadiazinone derivatives of the formula (I) according to the invention may be produced, for example, by the following reaction:

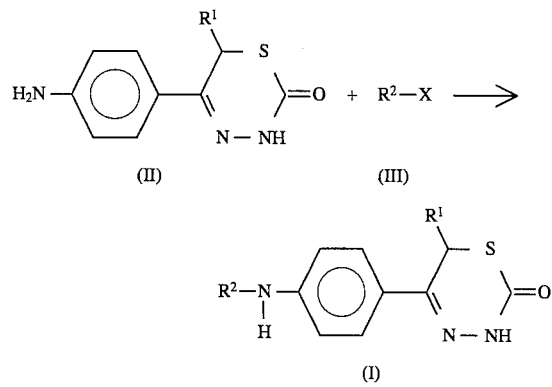

(wherein $R^1$ and $R^2$ are as defined before, and X is a halogen atom such as a chlorine atom and a bromine atom.)

Specifically, a compound of the formula (II) is reacted with a compound of the formula (III) by heating in an inactive solvent such as N,N-dimethylformamide, N,N-dimethylacetamide, or N-methyl-2-pyrrolidone at a temperature range from 50° to 200° C. for 0.5 to 10 hours to synthesize thiadiazinone derivatives of the formula (I). As a base, an organic base such as triethylamine and DBU (1,8-diazabicyclo[5.4.0]-7-undecene) or an inorganic base such as potassium carbonate and sodium carbonate may be added. As a catalyst, copper compounds such as metal copper, copper oxide, and copper chloride may be used.

The compound of the formula (II) utilized as a starting material may be synthesized by the following reaction:

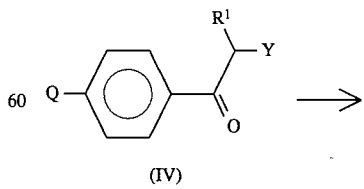

-continued

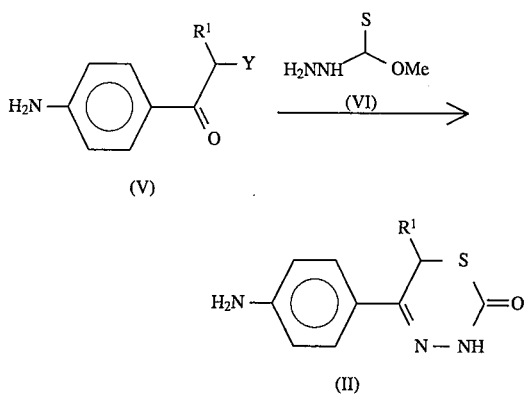

(wherein $R^1$ is as defined before, Q is amino substituted with protecting group such as acetyl and benzyloxycarbonyl; or a substituent such as nitro which can be converted into amino, and Y is a halogen atom such as chlorine and bromine).

In this reaction, when Q of the haloketone derivatives of the formula (IV) is amino which is substituted with a protecting group such as acetyl and benzyloxycarbonyl, the compound (IV) may be easily heated in a generally-utilized solvent such as methanol or ethanol containing proton acid such as hydrochloric acid or sulfuric acid at a temperature range from room temperature to 100° C. or less than the reflux temperature of the solvent for 0.5 to 20 hours in order to synthesize anilinohaloketone compounds of the formula (V) with the protecting group removed. When Q is a substituent such as nitro which can be converted into amino, the compound (IV) may be heated under an acidic condition in the presence of stannous chloride at a temperature range from room temperature to 100° C. or less than the reflux temperature of the solvent for 0.5 to 10 hours according to a general reduction in order to synthesize anilinohaloketone compounds of the formula (V).

Anilinohaloketone compounds of the formula (V) thus obtained may be reacted with thiocarbazine acid derivatives of the formula (VI) in an inactive solvent such as ethanol, tetrahydrofurane and acetonitrile at a temperature range from room temperature to 100° C. or less than the reflux temperature of the solvent for 0.5 to 10 hours in order to synthesize an objective intermediate of the formula (II). In this reaction, proton acid such as hydrochloric acid, sulfuric acid, p-toluenesulfonic acid, and trifluoroacetic acid may be added.

Thiadiazinone derivatives of the formula (I) may also be prepared in the following reaction:

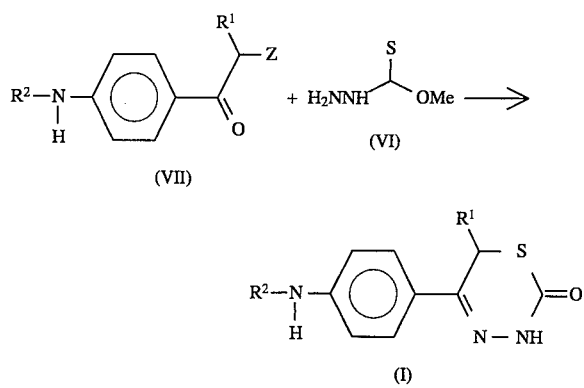

(wherein $R^1$ and $R^2$ are as defined before, and Z is a halopen atom such as chlorine and bromine.)

According to the reaction, haloketone of the formula (VII) is reacted with thiocarbazine acid derivatives of the formula (VI) by heating in an inactive solvent such as ethanol, THF, and acetonitrile at a temperature range from room temperature to 100° C. or less than the reflux temperature of the solvent for 0.5 to 10 hours to obtain an objective compound thiadiazinone derivatives of the formula (I). In this reaction, proton acid such as hydrochloric acid, sulfuric acid, p-toluenesulfonic acid, and trifluoroacetate may be added.

The compound of the formula (VII) which is a starting material of the foregoing reaction can be prepared according to the following reaction:

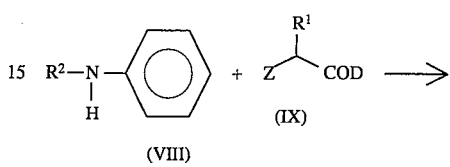

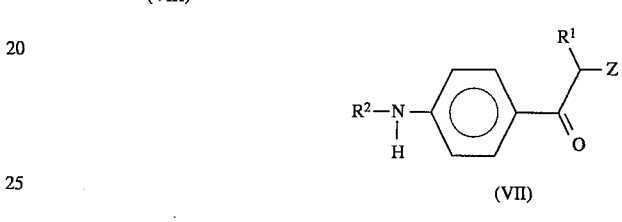

(wherein $R^1$, $R^2$, and Z are as defined before, D is a halogen atom such as chlorine and bromine, and Z and D are the same or different.)

According to the reaction, aniline derivatives of the formula (VIII) are reacted with acylhalide compounds of the formula (IX) by heating in an inactive solvent such as dichloromethane, dichloroethane, nitromethane, and trichlorobenzene in the presence of Lewis acid such as anhydrous aluminium chloride, anhydrous aluminium bromide, and anhydrous stannous chloride at a temperature range from ice water temperature to 100° C. or less than the reflux temperature of the solvent for 0.5 to 10 hours in order to synthesize haloketone derivatives of the formula (VII) which is an objective intermediate for the thidiazinone derivatives.

The compounds synthesized in this reaction can be separated and purified from the reaction mixture by a known method such as extraction, recrystallization, and chromatography.

The compounds according to the present invention have an excellent cardiotonic activity, and are useful as active ingredients of cardiotonic drugs which are used for the treatment of heart failure.

For pharmaceutical use, the compounds of the formula (I) obtained according to the present invention may be formulated as a composition containing appropriate carrier or vehicle which is generally utilized and is pharmaceutically acceptable, and may be appropriately administered orally or parenterally. For oral administration, the compounds are formulated in powder, granules, tablets, sugar-coat tablets, pills, capsules, liquid preparations, and the like. For parenteral administration, the compounds are formulated in suppository, suspension, liquid preparation, emulsion, ampule, injection, and the like. A combination of these formulations may also be utilized.

The above-mentioned formulations may be prepared by utilizing solid or liquid carriers, vehicles, or the like according to a known method.

Examples of solid carriers for formulation are lactose, kaolin, sucrose, crystallized cellulose, corn starch, talc, agar, pectin, stearic acid, magnesium stearate, lecithin, sodium chloride, and the like. Examples of the liquid carriers for formulation are glycerine, peanut oil, polyvinylpyrolidone, olive oil, ethanol, benzylalcohol, propyleneglycol, water, and the like.

The dose for administration may be determined by a physician according to a patient's age, gender, body weight, sensitivity, administration method, time and intervals for administration, disease degree, physical condition, formulation features, preparation, and kinds of an effective ingredient, and the like. For example, the compounds are orally administered at 1 to 10 mg/kg/day. However, dose should not be limited thereto.

EXAMPLES

The present invention will be explained in more detail by referring to the following examples. However, these examples should be regarded as an aid for concretely identifying the present invention and do not limit the scope of the invention.

Reference Example 1

Synthesis of 3,6-dihydro-5-(4-aminophenyl)-2H-1,3,4-thiadiazine-2-one (A) Synthesis of 4-acetylaminophenacyl chloride

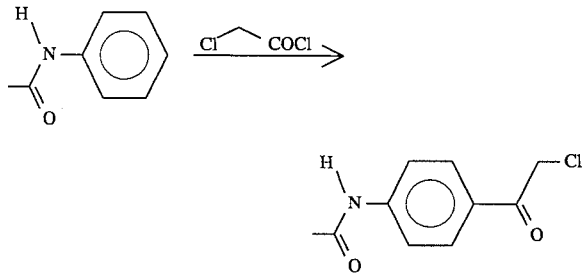

Acetanilde (10 g) and aluminium chloride (30 g) were suspended in 1,2,4-trichlorobenzene (50 mL), and heated at 70° C. by stirring with chloroacetyl chloride (6.5 mL) dropped. After dropping, the mixture was heated to 80° C., and stirred for one hour with the temperature maintained. The reacted mixture was poured into ice water (500 mL), followed by addition of hexane (100 mL) for filtration. The separated solid was further dissolved in a mixture solvent (ca. 700 mL) of ethyl acetate/THF (5:2), dried with anhydrous sodium sulfate, and subjected to a silica gel layer for filtration. The filtrate was finally concentrated under reduced pressure to obtain the captioned compound (14.14 g). Yield was 90.3%.

$^1$H-NMR (250 MHz, DMSO-$d_6$) δ:10.3 (1H, s) 7.94 (2H, d) 7.73 (2H, d) 5.12 (2H, s) 2.09 (3H, s)

(B) Synthesis of 4-aminophenacyl chloride

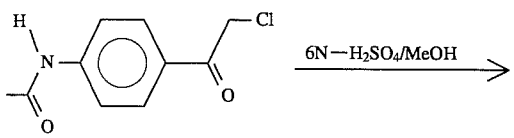

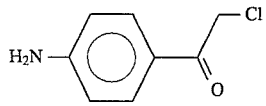

A mixture of 4-acetylaminophenacyl chloride (8.00 g), methanol (100 mL), and 6N-sulfuric acid (100 mL) was heated under reflux with stirring for 2.5 hours. The reacted solution was evaporated to remove methanol. To the concentrated substance, water(ca. 300 mL) was added for dilution, and saturated sodium carbonate solution was further added to prepare a weak basic solution. The precipitated solid was separated by filtration, and dried to obtain the captioned compound (7.32 g). Yield was quantitative.

$^1$H-NMR (250 MHz, CDCl$_3$) δ:7.81 (2H, d) 6.65 (2H, d) 4.61 (2H, s) 4.23 (2H, s)

(C) Synthesis of 3,6-dihydro-5-(4-aminophenyl)-2H-1,3,4-thiadiazine-2-one

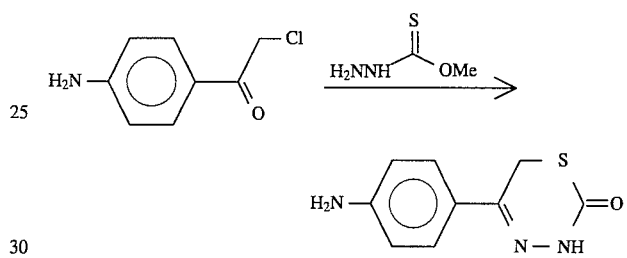

An acetonitrile solution (40 mL) containing 4-aminophenacyl chloride (1.53 g), trifluoroacetic acid (0.69 mL), and thiocarbazine acid O-methyl ester (1.05 g) was heated under reflux with stirring for four hours. The reacted mixture was cooled and diluted with water (ca. 200 mL). To the resultant solution, saturated sodium carbonate was added to prepare a weak basic solution. The precipitated viscous substance was extracted with ethyl acetate, and purified by a silica gel column chromatography (solvent: chloroform→ 8% THF/chloroform) to obtain the captioned compound (0.79 g). Yield was 42.3%.

$^1$H-NMR (250 MHz, DMSO-$d_6$) δ:11.29 (1H, s) 7.52 (2H, d) 6.58 (2H, d) 5.64 (2H, s) 4.07 (2H, s)

Example 1

Synthesis of 3,6-dihydro-5-[4-(4-pyridylamino)phenyl]-2H-1,3,4-thiadiazine-2-one

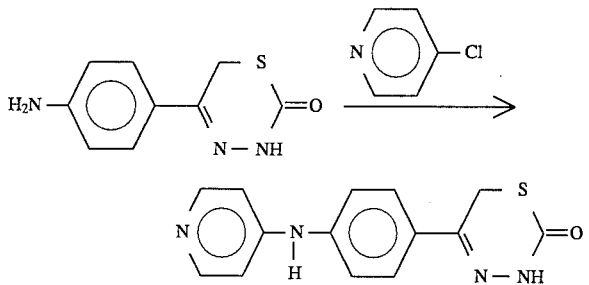

To a N-methyl-2-pyrrolidone solution (3 mL) containing 5-(4-aminophenyl)-2H-1,3,4-thiadiazine-2-one (0.27 g), triethylamine (90 μL) and 4-chloropyridine hydrochloride (0.20 g) were added in this order by heating at 100° C. with stirring, followed by further stirring with the temperature maintained for four hours. The reacted mixture was cooled and diluted with acetone (10 mL) and ether (15 mL). The precipitated crystal was separated by filtration, air-dried, dissolved in warm water (50 mL), and adjusted to pH8 with saturated potassium carbonate. The precipitated solid was separated by filtration, and purified by a silica gel column chromatography to obtain the captioned compound (0.26 g). Yield was 70.3%. melting point: 222° to 225° C. (decomposition)

1H-NMR (250 MHz, DMSO-$d_6$) δ:11.5 (1H, s) 9.10 (1H, s) 8.25 (2H, d) 7.79 (2H, d) 7.27 (2H, d) 7.00 (2H, d) 2.20 (2H, s)

Reference Example 2

Synthesis of
1-[4-(4-pyridylamino)phenyl]-2-chloropropanone

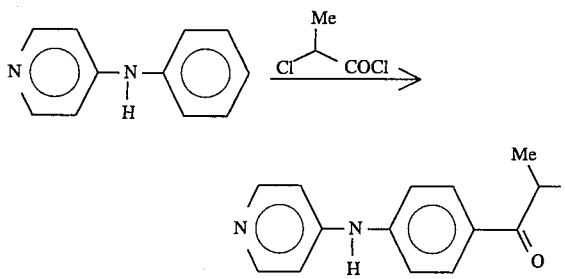

4-pyridylaminobenzene (9.00 g) and aluminium chloride (21 g) were suspended in 1,2,4-trichlorobenzene (45 mL). To the mixture solution, 2-chloropropionyl chloride (5.7 mL) was dropped by heating at 70° C. and stirring over ca. one minute. After dropping, the mixture was heated to 80° C., followed by reaction with the temperature maintained for one hour. The reacted mixture was diluted with dichloromethane (500 mL). Next, ice-water (20 mL) was carefully added to the solution, and sufficiently stirred. To the resultant solution, anhydrous potassium carbonate was added for drying until the viscosity of the solution disappeared. After the drying agent was removed by filtration, the solution was concentrated under reduced pressure to obtain a crude product. This product was finally purified by a silica gel column chromatography (solvent: chloroform→5% methanol/chloroform) to obtain the captioned compound (12.34 g). Yield was 89.5%.

$^1$H-NMR (250 MHz, DMSO-$d_6$) δ:9.41 (1H, s) 8.33 (2H, d) 8.00 (2H, d) 7.30 (2H, d) 7.10 (2H, d) 5.71 (1H, q) 1.61 (3H, d)

Example 2

Synthesis of
3,6-dihydro-5-[4-(4-pyridylamino)phenyl]-6-methyl-2H-1,3,4-thiadiazine-2-one

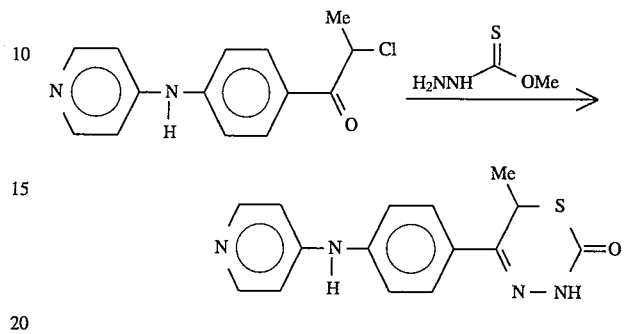

1-[4-(4-pyridylamino)phenyl]-2-chloropropanone (0.50 g) was dissolved in a mixture solvent of ethanol (5 mL) and 1N-hydrochloric acid (2.2 mL). To this solution, thiocarbazine acid O-methyl ester (0.23 g) was added, followed by heating under reflux for two hours. The reacted solution was then diluted with water, and adjusted to pH ca.8 with saturated potassium carbonate. The precipitated viscous substance was extracted with dichloromethane, and purified by a silica gel column chromatography (solvent: chloroform→5% methanol/chloroform) to obtain the captioned compound (0.30 g). Yield was 51%. melting point: 195° to 198° C. (decomposition)

$^1$H-NMR (250 MHz, DMSO-$d_6$) δ:11.6 (1H, s) 9.10 (1H, s) 8.24 (2H, d) 7.77 (2H, d) 7.26 (2H, d) 6.99 (2H, d) 4.71 (3H, d) 1.47 (3H, d)

Test Example

A pharmacological test on cardiotonic activity of the thiadiazinone derivatives according to the invention was conducted by utilizing papillary muscle sample enucleated from guinea pigs.

Male guinea pigs of 400–600 g body weight was beaten on the occiput portion. Immediately after that, the papillary muscle of the right ventricle was enucleated, and immobilized at the bottom of an organ bath which had been filled with Krebs-Henseleit solution and had been maintained at 32° C., with a mixture gas of $O_2$ and $CO_2$ (95%: 5%) flown. Next, the papillary muscle was fitted with a thread the end of which was connected to a trasducer in order to measure tension. A stationary tension of 0.5 g was loaded to the sample. The sample was then electrically driven with rectangular waves of 1.2 times that of a threshold through two platinum electrodes for one second every 2 seconds. The sample was thus prepared, and stabilized for 30 minutes. After that, each of the example compounds was added to the organ bath, and a reaction of the sample was recorded. Increase ratio of the papillary muscle contraction is shown in the following Table 1.

TABLE 1

| Compounds | Guinea pigs papillary muscle contraction | |
|---|---|---|
| | Dose (μM) | Increase ratio (%) |
| (Example 1) | 0.1<br>1.0 | 128<br>196 |
| (Example 2) | 0.1<br>1.0 | 90<br>128 |

Obviously, numerous modifications and variations of the present invention are possible in light of the above teachings. It is therefore to be understood that within the scope of the appended claims, the invention may be practiced otherwise than as specifically described herein.

What is claimed is:

1. A thiadiazinone compound of the formula

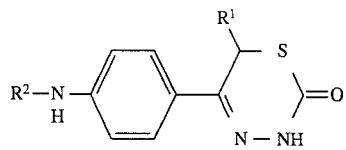

wherein $R^1$ represents hydrogen or $C_1$–$C_5$ alkyl, $R^2$ represents a 6-membered aromatic heterocyclic ring having 1–3 nitrogen atoms selected from the group consisting of pyridyl, pyridazinyl, pyrimidinyl, pyrazinyl and s-triazinyl which rings are unsubstituted or are substituted by one or more substituents selected from the group consisting of $C_1$–$C_5$ alkyl, cyano, hydroxy, $C_1$–$C_5$ alkoxy, amino, $C_1$–$C_5$ alkylamino, $C_2$–$C_5$ dialkylamino, $C_2$–$C_5$ alkylamino, $C_2$–$C_5$ acylamino, carboxyl, $C_2$–$C_5$ alkoxycarbonyl and carbamoyl; or a pharmaceutically acceptable salt thereof.

2. A compound according to claim 1, wherein the heterocyclic ring is pyridyl.

3. A compound according to claim 1, wherein $R^1$ is a hydrogen atom or methyl.

4. A compound according to claim 1, wherein $R^2$ is pyridyl and $R^1$ is a hydrogen atom.

5. A compound according to claim 1, wherein $R^2$ is pyridyl and $R^1$ is methyl.

6. A pharmaceutical composition comprising a therapeutically effective amount of a compound of claim 1 or a pharmaceutically acceptable salt thereof and a pharmaceutically acceptable carrier therefor.

7. A method of treating heart failure in humans, which comprises administering to a human in need of such treatment a therapeutically effective amount of a compound of claim 1 or a pharmaceutically acceptable salt thereof.

* * * * *